United States Patent [19]

Quinter et al.

[11] Patent Number: 4,916,725

[45] Date of Patent: Apr. 10, 1990

[54] PATIENT SUPPORT APPARATUS HAVING X-RAY FILM CARTRIDGE SHUTTLE POSITIONING MEANS

[75] Inventors: Rudolph F. Quinter, Troy; Michael L. Berger, Versailles; Jay L. Kuck, St. Marys, all of Ohio

[73] Assignee: Midmark Corporation, Versailles, Ohio

[21] Appl. No.: 149,750

[22] Filed: Jan. 29, 1988

[51] Int. Cl.⁴ .............................................. G03B 42/02
[52] U.S. Cl. .................................... 378/177; 378/181; 378/205; 378/209; 5/60; 33/809
[58] Field of Search .................... 378/167, 177–181, 378/208, 209, 205; 5/60, 81 R, 82 R; 269/322–323, 307, 328; 33/161

[56] References Cited

U.S. PATENT DOCUMENTS

| | | | |
|---|---|---|---|
| 992,205 | 5/1911 | Kelley | 378/167 |
| 1,050,733 | 1/1913 | Greathead | 33/161 |
| 1,272,976 | 7/1918 | McLucas | 33/161 |
| 1,299,627 | 4/1919 | Simon | 33/161 |
| 1,933,682 | 11/1933 | Perry et al. | 269/307 |
| 2,989,634 | 6/1961 | Ould et al. | 378/177 |
| 3,492,729 | 2/1970 | Crain | 33/161 |
| 3,826,922 | 7/1974 | Ingles | 378/181 |
| 4,097,746 | 6/1978 | Ingham et al. | 378/177 |
| 4,166,459 | 9/1979 | Nightingale | 269/328 |
| 4,193,148 | 3/1980 | Rush | 378/177 |
| 4,651,364 | 3/1987 | Hayton et al. | 5/60 |
| 4,691,393 | 9/1987 | Kuck | 5/62 |

Primary Examiner—Craig E. Church
Assistant Examiner—John C. Freeman
Attorney, Agent, or Firm—Biebel, French & Nauman

[57] ABSTRACT

The present invention relates to a patient support apparatus useful during x-raying. The apparatus includes a frame having a graduated scale along the length of at least one side thereof. The frame has means for supporting an x-ray film cartridge shuttle thereon and permitting movement of the x-ray film cartridge shuttle along the length of the frame. The apparatus also includes a rod for positioning the x-ray film cartridge shuttle along the length of the frame. The rod has a graduated scale along the length thereof. The units of the graduated scale of the rod correspond to the units of the graduated scale of the frame.

7 Claims, 5 Drawing Sheets

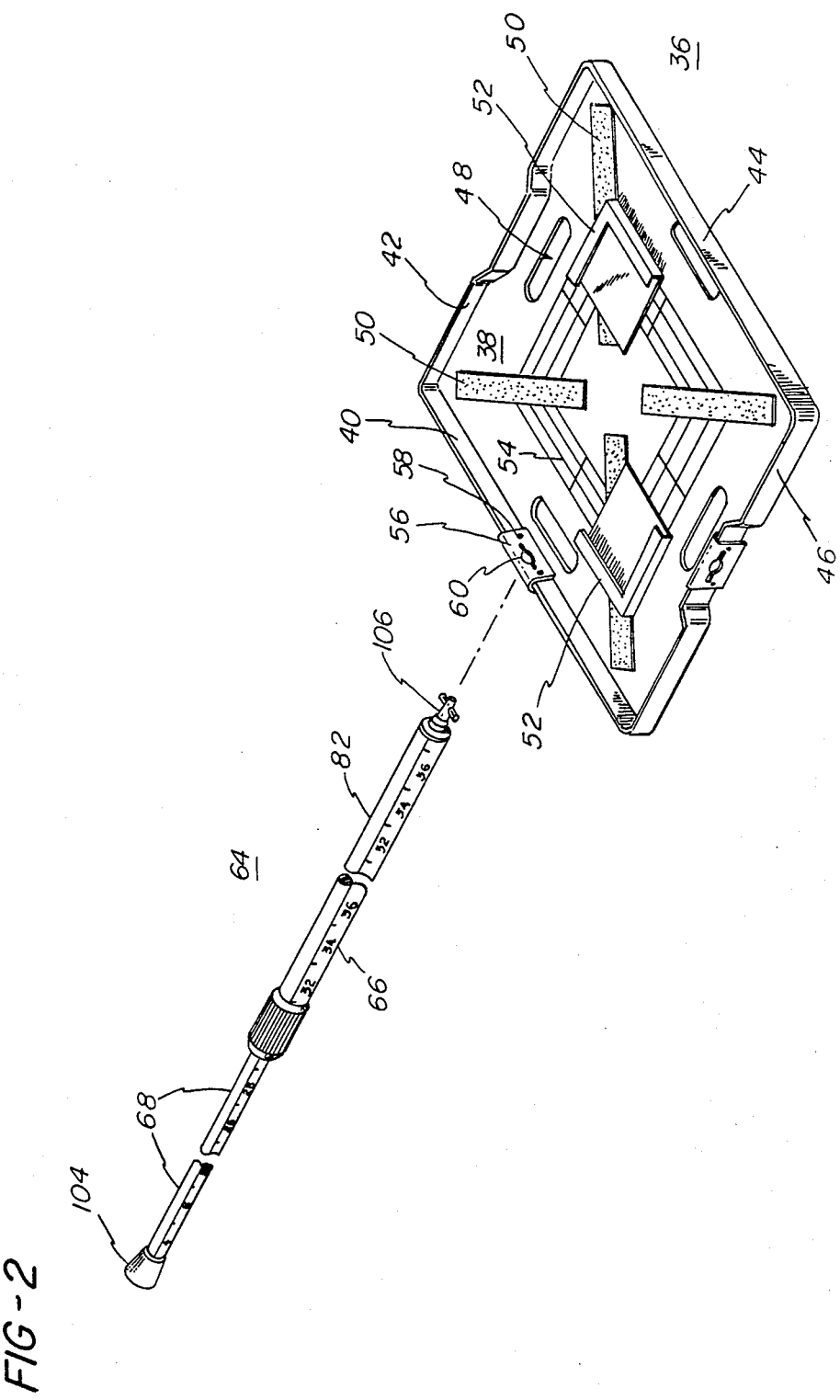

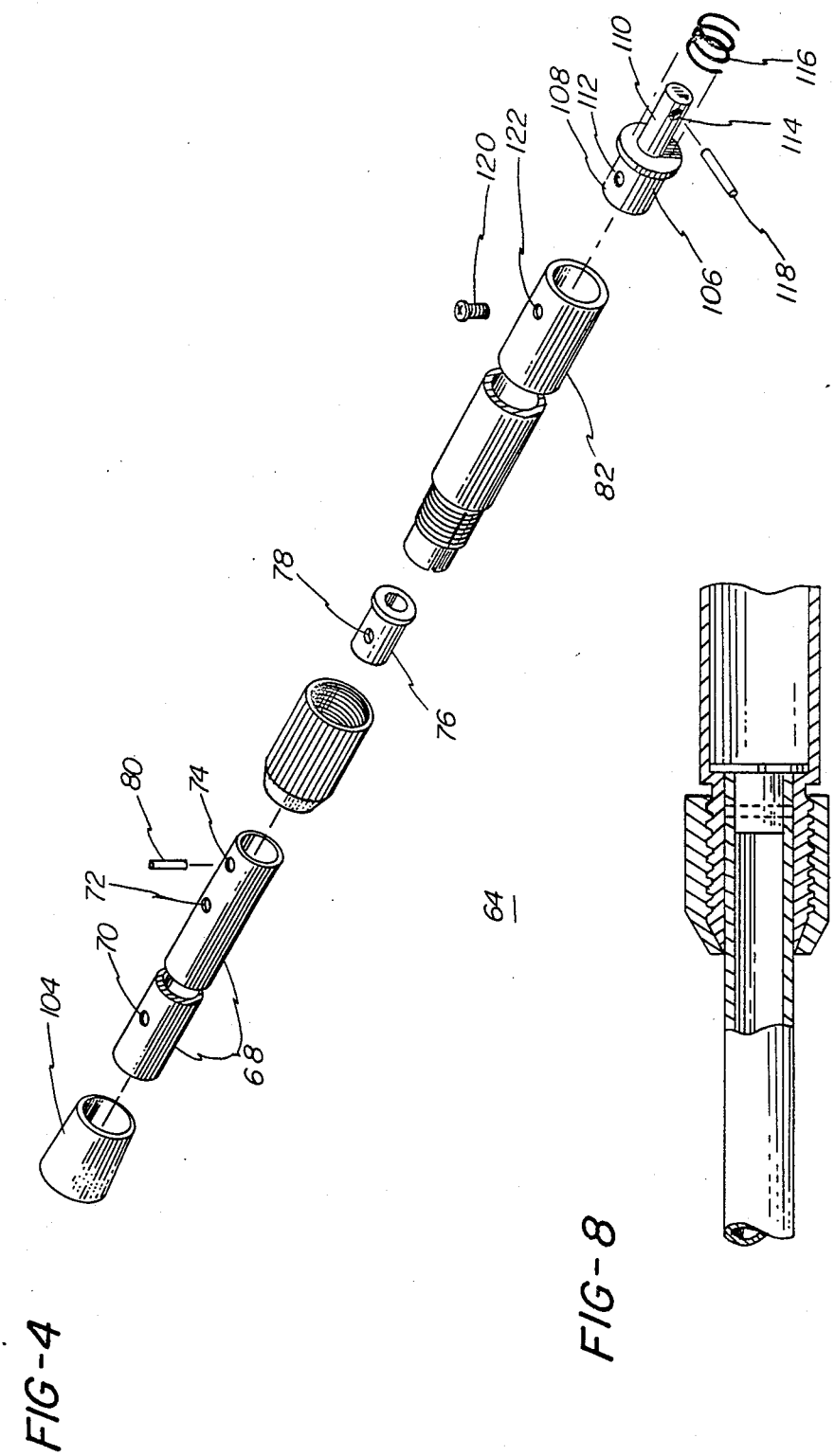

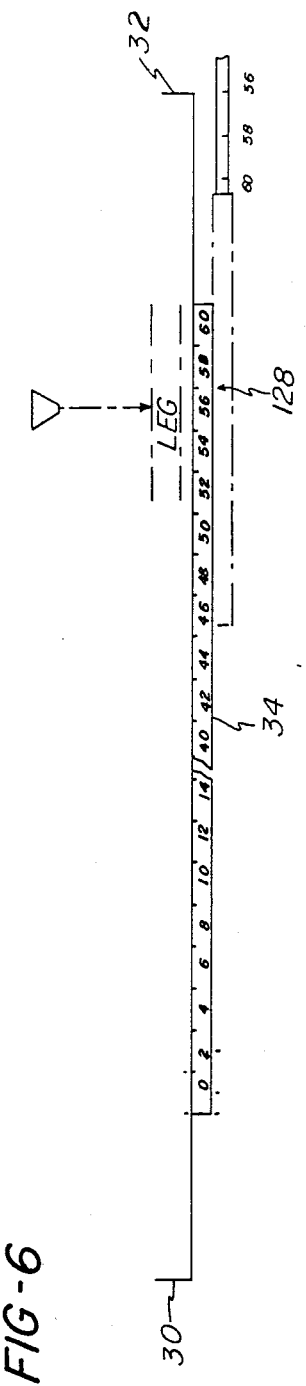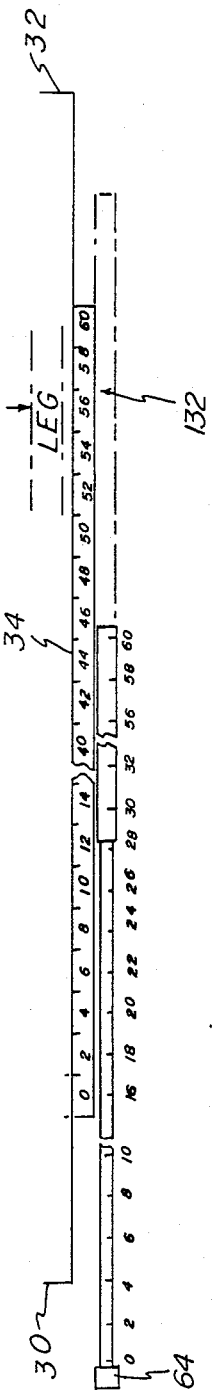
FIG-6
FIG-7

PATIENT SUPPORT APPARATUS HAVING X-RAY FILM CARTRIDGE SHUTTLE POSITIONING MEANS

BACKGROUND OF THE INVENTION

The present invention relates to a patient support apparatus, and more particularly, to a patient support apparatus having x-ray film cartridge shuttle positioning means for use in the health care industry.

Various types of bed-like equipment are commonly used in hospitals and other health care facilities. One type of such equipment is referred to as a stretcher which is normally provided with wheels for ease of movement and used in a variety of situations. Such a stretcher is disclosed in commonly assigned U.S. Pat. No. 4,691,393. The wheeled stretcher may be used in emergency room settings and in general hospital service for transporting patients from one location to another. Such a stretcher is of relatively heavy-duty construction and includes a base supported by a plurality of wheels. The base supports the stretcher frame to which a bed portion is attached. The stretcher is also normally provided with side rails which may be selectively raised or lowered. The rails securely hold the patient on the stretcher, but can also be moved out of the way to enable the patient to move or be moved from or onto the stretcher.

Particularly, when used in the emergency room, the wheeled stretcher fulfills a variety of roles. For example, the stretcher may serve as a bed during a period of time when a patient is awaiting treating. The stretcher can also be used to transport the patient. Frequently, the stretcher also serves as an examination table or even as a surgical table for treatment of the patient.

If properly equipped, the wheeled stretcher may serve as an x-ray table for taking x-rays of patients before, during, or after surgical operations. Typical stretchers which can serve as x-ray tables have an x-ray film cartridge support which is located beneath an x-ray transparent horizontal bed surface. Stretchers having x-ray film cartridge shuttles which are slidably movable beneath horizontal bed surfaces are taught in U.S. Pat. Nos. 2,989,634; 4,193,148; and 4,651,364.

A positioning rod having an end hook is used to engage the end handle of the x-ray film cartridge shuttle of U.S. Pat. No. 2,989,634 in order to position the shuttle on the hospital table. Graduations are provided on the rod so that the x-ray film cartridge shuttle can be located in the same position for a succession of photographs. Difficulty arises, however, when the x-ray film cartridge shuttle has to be moved to a new position on the table. When a technician stands at the end of the hospital table and holds the rod engaged with the end handle of the shuttle, he either has to guess as to the distance over which the rod is to be pushed in order to reposition the shuttle or push the rod, look at the shuttle position from the side of or underneath the table, and if necessary again push the rod. Such shuttle positioning can interfere with the activities of the doctors and nurses who are working on the patient on the hospital table and also be time consuming. This is particularly a problem in cases where a stretcher is used as the x-ray table, since such cases usually involve emergency situations where the trauma team must remain close to the patient.

Thus the need exists in the art for an x-ray film cartridge shuttle positioning means which results in an accurate positioning of the x-ray film cartridge shuttle relative to the patient and does not interfere with the work of the trauma team on the patient on the hospital table.

SUMMARY OF THE INVENTION

The present invention provides a patient support apparatus useful during the x-raying of the patient. The apparatus comprises a frame for supporting a bed surface. The frame has a length and a width and a head end and a foot end.

The frame has a graduated scale along the length of at least one side thereof. Preferably, the frame has a graduated scale along the lengths of both sides thereof. As long as the scale is graduated, the scale can be in any units, e.g., inches or centimeters, as desired. The frame graduated scale can increase numerically from the head end to the foot end or from the foot end to the head end. A base supports the frame.

The apparatus also comprises an x-ray film cartridge shuttle. The frame has means for supporting the x-ray film cartridge shuttle beneath the bed surface and permitting movement of the x-ray film cartridge shuttle along the length of the frame.

The apparatus also comprises a rod for positioning the x-ray film cartridge shuttle along the length of the frame. The first end of the rod has means for engaging the x-ray film cartridge shuttle. The second end of the rod has a handle thereon. The rod has a graduated scale along the length thereof. The units of the graduated scale of the rod correspond to the units of the graduated scale of the frame. The rod graduated scale can increase numerically from the handle end to the engaging means end or from the engaging means end to the handle end.

Briefly, the apparatus is used as follows. Assume that the frame graduated scale increases numerically from the head end to the foot end, the rod graduated scale increases numerically from the handle end to the engaging means end, and the rod is to position the x-ray film cartridge shuttle from the frame foot end. By looking at the frame scale from the side of the apparatus, the technician determines the frame scale number which corresponds to the body section to be x-rayed. The technician then walks to the frame foot end, engages the rod with the x-ray film cartridge shuttle whose center corresponds to the last number of the frame scale, and pushes the rod, and thus, the x-ray film cartridge shuttle until the rod scale number which corresponds with the determined frame scale number appears in line with the end of the frame.

As such, the present apparatus provides for accurate positioning of the x-ray film cartridge shuttle on a hospital table. Also, the technician can position the shuttle from one end of the frame without disturbing the trauma team.

Accordingly, objects of the present invention are to provide an x-ray film cartridge shuttle positioning means whose operation results in an accurate positioning of the x-ray film cartridge shuttle on a hospital table relative to the patient, does not interfere with the trauma team's work, and is not time consuming.

Other objects and advantages of the present invention will be apparent from the following description, the accompanying drawings, and the appended claims.

BRIEF DESCRIPTION OF THE DRAWINGS

FIG. 1A is an enlarged view of the head end of the patient support apparatus of FIG. 1;

FIG. 1B is an enlarged view of the foot end of the patient support apparatus of FIG. 1;

FIG. 2 is a three-quarter view of the rod and x-ray film cartridge shuttle of the present invention;

FIG. 4 is a three-quarter view of the rod shown partially exploded;

FIG. 6 is a schematic side view of the frame of FIG. 1, x-ray film cartridge shuttle, and rod wherein the rod is being used from the foot end of the frame;

FIG. 7 is a schematic side view of the frame, x-ray film cartridge shuttle, and rod wherein the rod is being used from the head end of the frame; and FIG. 8 is a sectional view of the portion of the rod whereat the telescoping sections are joined.

DETAILED DESCRIPTION OF THE PREFERRED EMBODIMENTS

The present invention is generally applicable to a patient support apparatus typically found in hospital emergency rooms and other hospital environments. The present invention provides a patient support apparatus having an x-ray film cartridge shuttle positioning means.

Figure 1:
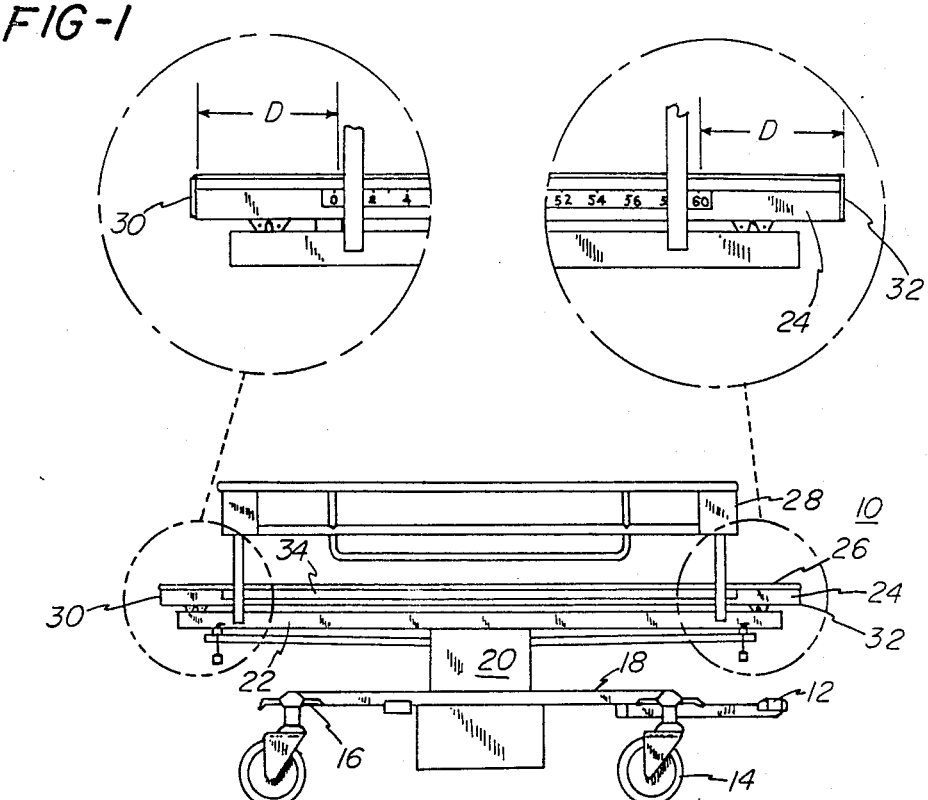
FIG. 1 is a side view of the patient support apparatus of the present invention.

Referring generally to FIG. 1, a patient support apparatus 10 is shown as having a wheeled base including supportive cross members 12. A wheel assembly 14 is provided at each end of the members 12, and a brake mechanism 16, the structure of which is well known in the art, is provided for locking the wheels to prevent movement of patient support apparatus 10 when desired. Cross members 12 are connected by a base plate 18 which supports a hollow vertical column 20.

Column 20 is connected by an axle (not shown) to a frame 22. The frame 22 supports bed surface 24 upon which an appropriate mattress 26 is placed. The bed surface 24 and mattress 26 are selected to be x-ray transparent.

To prevent a patient occupying patient support apparatus 10 from accidentally falling from the apparatus, a side rail assembly 28 is provided along each side of the apparatus. Only a single side rail is shown in FIG. 1 for purposes of clarity. However, it will be understood that identical and complete side rail assemblies 28 are mounted in identical fashion to each side of the apparatus.

The frame 22 has a head end 30 and a foot end 32. The frame 22 also has a graduated scale 34 along the length of at least one side thereof. Although not illustrated, the frame 22 preferably has a graduated scale 34 along the lengths of both sides. As long as the scale is graduated, the scale can be in any desired units, e.g., centimeters or inches. For illustration purposes, a scale having 60 units is used herein. The scale 34 can increase numerically from the head end to the foot end (illustrated) or from the foot end to the head end (not illustrated). The detail of the graduated scale 34 is seen more clearly in FIG. 6.

A decal having a graduated scale thereon is a useful way to apply the scale to the frame 22. At the head end 30 as shown in FIG. 1A, the graduated scale 34 begins on the frame 22 at a distance D from the end of the frame. The distance D is equal to one-half of the length of the x-ray film cartridge shuttle which will be discussed later. Likewise at the foot end 32 as shown in FIG. 1B, the graduated scale 34 ends on the frame 22 at a distance D from the end of the frame. Again, the distance D is equal to one-half of the length of the x-ray film cartridge shuttle. In this manner, positioning of the x-ray film cartridge shuttle is relative to the center of the shuttle, and thus, to the center of the x-ray film cartridge thereon.

Referring now to FIG. 2, the x-ray film cartridge shuttle 36 has a bottom 38 and sides 40, 42, 44, and 46. The bottom 38 has handle slots 48 therein for easily transporting the shuttle 36. The bottom 38 has a plurality of fasteners 50 thereon. A useful fastener is VELCRO (a registered trademark) which is commercially avilable from Velcro USA Inc.

Corner brackets 52 are used for holding an x-ray film cartridge (not shown) on the shuttle 36. The corner brackets 52 are placed on the fasteners 50 so that the mounted x-ray film cartridge is centered on the shuttle 36; a grid 54 on the bottom 38 is useful for this purpose. The corner brackets 52, which are preferably made of aluminum, are attached to the fasteners 50 by means of VELCRO strips attached to the back of corner brackets 52 (not shown).

A keyway 56 is attached to side 40 by rivets 58. The keyway 56 has an aperture 60 therein.

A second keyway 57 may be provided at a right angle to keyway 56 along side 46 of the shuttle 36 to enable the same shuttle to be used with a stretcher having a narrower bed surface. Also, while not shown, further keyways may be provided on sides 42 and 44 of the shuttle, so that the orientation of the shuttle will be immaterial for use as will be described.

Figure 3:
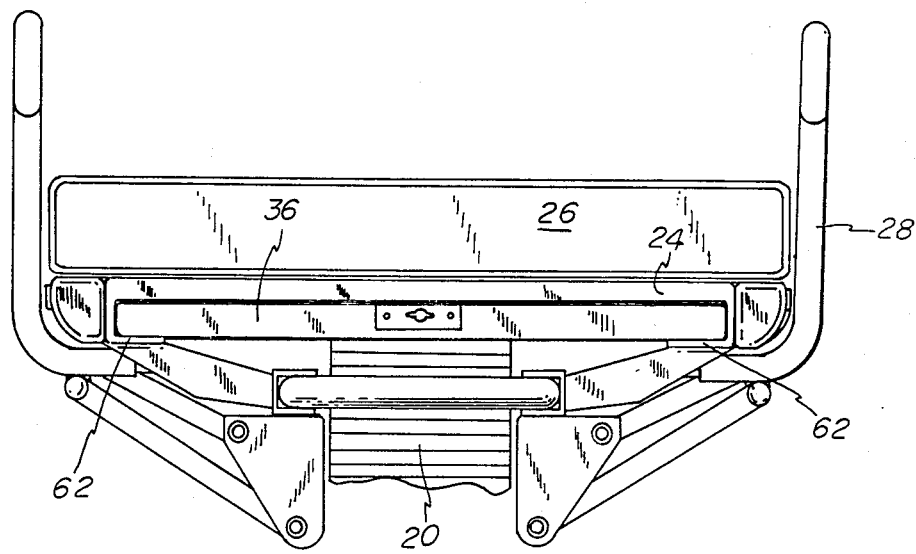
FIG. 3 is an end view of the patient support apparatus.

As shown in FIG. 3, the stretcher frame 22 has means for supporting the x-ray film cartridge shuttle 36 thereon and permitting movement of the x-ray film cartridge shuttle 36 along the length of the frame 22. The means for supporting the x-ray film cartridge shuttle 36 preferably comprises two tracks 62 which extend the length of the frame 22. After an x-ray film cartridge is loaded into the shuttle 36, the shuttle 36 is fed beneath the bed surface 24 and onto the tracks 62. The x-ray film cartridge shuttle 36 can then be moved freely on the tracks 62.

A rod 64 for positioning the x-ray film cartridge shuttle 36 beneath the stretcher bed surface along the length of frame 22 is shown in FIG. 2. The rod 64 has a graduated scale 66 along the length thereof. The units of the graduated scale 66 of the rod 64 correspond to the units of the graduated scale 34 of the frame 22. Preferably, the rod 64 is telescoping, although a unitary rod may be used.

In order to better understand the construction of rod 64, reference is made to FIG. 4 where the rod 64 is illustrated without the scale 66 thereon for the sake of simplicity. The rod 64 includes an inner tube 68 and a tubing insert 76 having a hole 78 therein, which is placed inside inner tube 68 and attached thereto by pin 80 cooperating with a hole 74.

An outer tube 82 has at one end thereof a narrowed, threaded portion 84 and a leading portion 86 including at least one slot 88. A lock ring 90 having a threaded interior is placed over threaded portion 84. As seen in FIG. 8, tubing insert 76 prevents inner tube 68 from being removed from outer tube 82, but permits telescoping movement of the inner tube within the outer tube. Lock ring 90 cooperates with threaded portion 84 in a manner well known in the art and used commonly, for example, with microphone stands, to secure inner tube 68 with respect to outer tube 82, thereby fixing the rod at either its minimum or its maximum length. Of course, other appropriate means for locking the telescoping rod at its minimum and maximum lengths can be used, and will be readily apparent to those skilled in the art.

An end cap 106 is provided at the end of outer tube 82 opposite threaded portion 84. End cap 106 comprises a large diameter portion 108 and a small diameter portion 110. Large diameter portion 108 has a hole 112 therein while small diameter portion 110 has a hole 114 therethrough. A spring 116 is placed around small diameter portion 110 and a roll pin 118 is inserted through hole 114 so as to keep spring 116 on small diameter portion 110. Shuttle end 106 is used for engaging x-ray film cartridge shuttle 36 as will be discussed later. Shuttle end 106 is attached to outer tube 82 by a screw 120 through holes 122 and 112. Graduated scale 66 can increase numerically from the handle end to the shuttle end or from the shuttle end to the handle end.

Referring to FIG. 2, keyway 56 has an aperture 60 whose shape corresponds to the cross-section of the small diameter portion 110 at the roll pin 118. Although not illustrated, shuttle end 106 of rod 64 engages x-ray film cartridge shuttle 36 as follows. Small diameter portion 110 having roll pin 118 therethrough is inserted through aperture 60 of keyway 56. The rod 64 is then rotated by about 90°; spring 116 prevents disengagement of rod 64 from shuttle 36.

Figure 5:
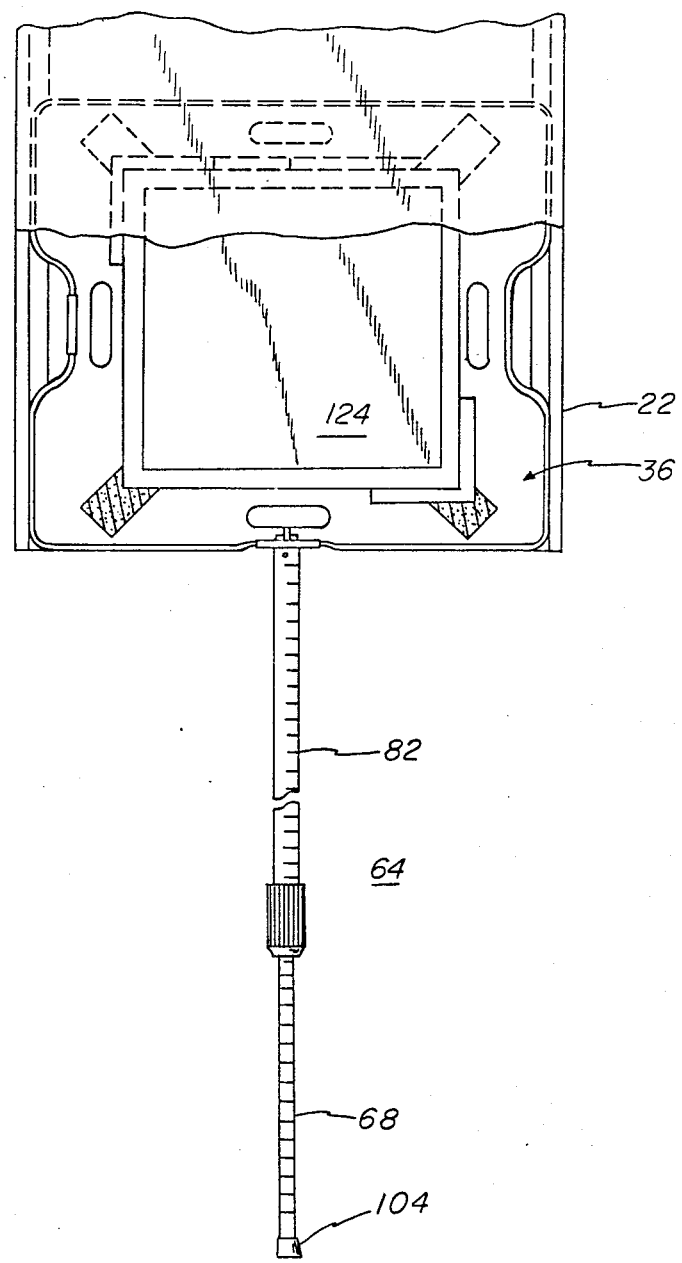
FIG. 5 is a top view of the foot end of the frame of FIG. 1, the x-ray film cartridge shuttle, and rod.

An example of how to use the present apparatus follows. An x-ray film cartridge 124 is loaded onto the x-ray film cartridge shuttle 36 as shown in FIG. 5. The loaded x-ray film cartridge shuttle 36 is then slid onto the tracks 62 from the foot end 32 as shown in FIG. 3 and the end of shuttle 36 is lined up with the end of frame 22 as shown in FIG. 5. The rod 64 then engages x-ray film cartridge shuttle 36. The rod graduated scale 66 increases from the handle end to the shuttle end.

The physician then determines what frame graduated scale number corresponds to the patient area to be x-rayed and tells the technician. For example, assume that the patient's leg 126 is to be x-rayed as shown in FIG. 6. By looking at frame graduated scale 34, the physician determines that frame scale number "56" corresponds to the patient's leg 126 and informs the technician. The technician then pushes rod 64 until rod scale number "56" is lined up with the end of the frame 22. In some situations, the technician may be responsible for determination of the frame scale number. Although the rod scale 66 appears in the side view of FIG. 6, the rod scale 66 is typically placed on the rod 64 so that the scale appears from a top view. Thus the technician can stand at the end of the frame 22 and push rod 64 while looking down at rod scale 66. When rod scale 66 reads "56", the x-ray film cartridge shuttle 36 is centered at frame scale number "56" as shown by arrow 128. The technician then takes x-rays of leg 126 by using a commercially available x-ray source 130 to direct x-rays onto the leg 126.

In another example of how to use the present apparatus as shown in FIG. 7, the loaded x-ray film cartridge shuttle 36 is slid onto the tracks 62 from the head end 30 of the frame 22. The rod graduated scale 66 increases from the handle end to the shuttle end. Again, assume that the patient's leg 126 is to be x-rayed and that the technician determines that frame scale number "56" corresponds to the patient's leg 126.

Because the technician is pushing rod 64 from the head end 30 of the frame 22, he must deduct frame scale number "56" from 60, the total number of units both on the frame 22 and the rod 64, in order to arrive at the corresponding rod scale number, i.e., "4". The technician then pushes rod 64 unitl rod scale number "4" is lined up with the end of the frame 22. When the rod scale 66 reads "4", the x-ray film cartridge shuttle 36 is centered at frame scale number "56" as shown by arrow 132. The technician then takes x-rays of leg 126 by using a commercially available x-ray source 130 to direct x-rays onto leg 126.

Of course, the need to subtract when positioning of the shuttle is made from the end not normally used can be avoided by placing two scales on the side frame of the stretcher. The two scales can be distinguished by designating and labelling one as the "head" scale and the other as the "foot" scale. Other techniques, such as providing the scales in contrasting colors, can also be used. Alternately, a single scale can be provided on the stretcher, with two, opposite-running scales being provided on the rod.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A patient support apparatus useful during x-raying comprising:
   a frame for supporting a bed surface having a length and a width and a head end and a foot end wherein said frame has a graduated scale along the length of at least one side thereof;
   a base for supporting said frame;
   an x-ray film cartridge shuttle;
   means located on said frame for supporting said x-ray film cartridge shuttle thereon and permitting movement of said x-ray film cartridge shuttle along the length of said frame;
   a rod for positioning said x-ray film cartridge shuttle along the length of said frame wherein said rod has a graduated scale along the length thereof and the units of said graduated scale of said rod correspond to the units of said graduated scale of said frame;
   a first end of said rod having means for engaging said x-ray film cartridge shuttle; and
   said engaging means comprising:
   a pin inserted through the diameter of said first end of said rod; and
   a spring surrounding the diameter of said first end of said rod.

2. The patient support apparatus of claim 1 wherein the first end of said x-ray film cartridge shuttle has an aperture having a shape corresponding to the cross-section of said rod and pin inserted through said rod.

3. In a patient support apparatus useful during x-raying comprising a frame for supporting a bed surface having a length and a width and a head end and a foot end, a base for supporting said frame; an x-ray film cartridge shuttle; means located on said frame for supporting said x-ray film cartridge shuttle thereon and permitting movement of said x-ray film cartridge shuttle along the length of said frame; and a rod for positioning said x-ray film cartridge shuttle along the length of said frame, the improvement comprising:
  means defining a graduated scale along the length of at least one side of said frame, and means defining a corresponding graduated scale along the length of said rod such that a technician standing at an end of said frame may precisely position said shuttle to a selected position along said frame, as determined from a selected point on said scale along said frame, by reference to a corresponding point on said scale along said rod.

4. The patient support apparatus of claim 3 wherein said frame has a graduated scale along the lengths of both sides thereof.

5. The patient support apparatus of claim 3 wherein said graduated scale numerically increases from the head end to the foot end.

6. The patient support apparatus of claim 3 wherein said graduated scale numerically increases from the foot end to the head end.

7. The patient support apparatus of claim 3 further including a pair of independent scales having identical units of length, said scales being provided along a single side of said frame, and wherein a first of said scales numerically increases from the head end to the foot end, and a second of said scales numerically increases from the foot end to the head end.

* * * * *